(12) United States Patent
Abdel-Meguid et al.

(10) Patent No.: US 10,820,982 B2
(45) Date of Patent: Nov. 3, 2020

(54) METHOD OF BLADDER AUGMENTATION WITH MODIFIED ILEAL SEGMENT AND BIOLOGICALLY COMPATIBLE TISSUE

(71) Applicant: King Abdulaziz University, Jeddah (SA)

(72) Inventors: Taha Abo-Almagd Abdel-Meguid, Jeddah (SA); Abdulmalek Mohammad Saeed Tayib, Jeddah (SA); Ahmad Jalal Al-Sayyad, Jeddah (SA); Truki E. Altayloni, Jeddah (SA); Mohammed K. Khan, Jeddah (SA); Ahmed S. Zugail, Jeddah (SA)

(73) Assignee: King Abdulaziz University, Jeddah (SA)

( * ) Notice: Subject to any disclaimer, the term of this patent is extended or adjusted under 35 U.S.C. 154(b) by 268 days.

(21) Appl. No.: 15/180,984

(22) Filed: Jun. 13, 2016

(65) Prior Publication Data

US 2017/0196674 A1   Jul. 13, 2017

Related U.S. Application Data

(60) Provisional application No. 62/277,626, filed on Jan. 12, 2016.

(51) Int. Cl.
*A61F 2/04* (2013.01)
*A61B 17/11* (2006.01)

(52) U.S. Cl.
CPC .............. *A61F 2/042* (2013.01); *A61B 17/11* (2013.01); *A61F 2250/0067* (2013.01)

(58) Field of Classification Search
CPC ... A61F 2/042; A61F 2250/0067; A61B 17/11
See application file for complete search history.

(56) References Cited

FOREIGN PATENT DOCUMENTS

| CN | 104352255 A | 2/2015 |
|---|---|---|
| RU | 2 323 688 C1 | 5/2008 |
| RU | 2 371 102 C1 | 10/2009 |

OTHER PUBLICATIONS

Abou-Elela. "Augmentation Cystoplasty: in Pretransplant Recepients." Understanding the Complexities of Kidney Transplantation, 2011, pp. 270-330.*

(Continued)

*Primary Examiner* — Suba Ganesan
*Assistant Examiner* — Aren Patel
(74) *Attorney, Agent, or Firm* — Oblon, McClelland, Maier & Neustadt, L.L.P.

(57) ABSTRACT

A method of augmenting a bladder including incising a native bladder to form an incised native bladder, implanting a tissue flap, which includes a bladder-expansion portion connected to a tubular portion; and suturing the bladder-expansion portion to an edge of the incised native bladder. The method forms an augmented bladder with a volume capacity that is 100%-250% larger than a volume capacity of the native bladder. The tissue flap may be a modified ileal segment or a biologically compatible tissue flap. The biologically compatible tissue flap having a biocompatible scaffold which includes a collagen mesh, which is coated by a biochemical factor, a cell derived matrix, and/or a synthetic biocompatible polymer. The biologically compatible tissue flap is configured with the bladder-expansion portion and a tubular portion.

18 Claims, 3 Drawing Sheets

(56) References Cited

OTHER PUBLICATIONS

Studer et al. Twenty Year Experience with an Ileal Orthotopic Low Pressure Bladder Substitute—Lessons to Be Learned. The Journal of Urology, vol. 176, No. 1, 2006, pp. 161-166.*
Friedman et al. Split-Cuff Nipple Technique of Ureteral Reimplantation in Children With Thick-Walled Bladders Due to Posterior Urethral Valves. Urology, vol. 85, No. 1, 2015, pp. 199-204.*
Radiopaedia_NPL_https://radiopaedia.org/articles/ileum (accessed Feb. 8, 2018).*
Bollinger et al. "Biofilms in the Large Bowel Suggest an Apparent Function of the Human Vermiform Appendix." Journal of Theoretical Biology, vol. 249, No. 4, 2007, pp. 826-831.*
Möllhoff et al. "Spontaneous Perforation of Augmented Bladder after Exstrophy Repair." Urologia Internationalis, vol. 47, No. 3, 1991, pp. 167-168.*
Baka-Ostrowska et al. "Bladder Augmentation and Continent Urinary Diversion in Boys with Posterior Urethral Valves." Central European Journal of Urology, vol. 64, 2011, pp. 237-239 (Year: 2011).*
Ashraf Abou-Elela, "Augmentation Cystoplasty: in Pretransplant Recepients", Understanding the Complexities of Kidney Transplantation, www.intechopen.com, Chapter 14, Sep. 2011, pp. 279-330.
Stefan Beyerlein, et al., "The Double Dutch Technique: Split Ileal Graft and Double Monti Tube in Ileocystoplasty", Journal of Pediatric Urology, vol. 6, Supplement 1, Apr. 2010, p. S43 (Abstract only).
A. A. Shokeir, "Interposition of ileum in the ureter: a clinical study with long-term follow-up", British Journal of Urology, vol. 79, 1997, pp. 324-327.
Abdulmalik M S Tayib, et al., "Novel augmentation ileocystoplasty technique to manage non-compliant bladders in the presence of obstructed megaureters: The fez procedure", International Journal of Urology, vol. 22, 2015, pp. 301-305.
Tayib, A.M.S., et al., "A novel "fez procedure" for non-compliant bladders and obstructed megaureters: Augmentation ileocystoplasty and ureteral reimplantation into ileal loop", European Association of Urology (EAU)—Events, Oct. 12, 2013, 2 pages (Abstract only).

* cited by examiner

METHOD OF BLADDER AUGMENTATION WITH MODIFIED ILEAL SEGMENT AND BIOLOGICALLY COMPATIBLE TISSUE

CROSS REFERENCE TO RELATED APPLICATIONS

This application claims the benefit of U.S. Provisional Application No. 62/277,626 filed Jan. 12, 2016, the entire contents of which are incorporated herein by reference.

BACKGROUND OF THE INVENTION

Technical Field

The present invention relates to a surgical method to augment a bladder and direct ureteroileal anastomosis with either a modified ileal segment or a regenerated biocompatible tissue construct.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Augmentation cystoplasty was first applied in humans in 1889 by von Mikulicz, but it was later popularized by Couvelaire in the 1950s, SeeVon Mikulicz J. "Zur operation der angebarenen blaBen-Spalte." Zentralbl. Chir. 1889; 20: 641-3; Couvelaire R. "La petite vessie des tuberculeux genito-urinaires: essai de classification, places et variantes des cysto-intestinoplasties." J. Urol. (Paris) 1950; 56: 381-434, each incorporated herein by reference in their entirety. Clean intermittent catheterization (CIC) contributed widely to the use of augmentation cystoplasty in the 1980s. See Bramble F J. "The treatment of adult enuresis and urge incontinence by enterocystoplasty." Br. J. Urol. 1982; 54: 693-6, incorporated herein by reference in its entirety. One important aim in the setting of augmentation cystoplasty is to create a low-pressure reservoir, while preserving die integrity of the upper urinary tract and improving incontinence. See Biers S M, Venn S N, Greenwell T J. "The past, present and future of augmentation cystoplasty." BJU Int. 2012; 109: 1280-93, incorporated hereinby reference in its entirety. Several tubular or detubularized bowel segments have been used successfully for bladder augmentation, including cecum, ascending colon and sigmoid colon. Yet, ileocystoplasty is the most preferred cystoplasty procedure. Although the new pharmacotherapies, intravesical injections of botulinum toxin-A and neuromodulations, have led to a downward trend for augmentation cystoplasty over the past decade, this procedure remains a viable option for non-compliant bladders refractory to these treatments.

Traditionally, obstructed megaureters have been treated by tailoring and reimplantation of the ureters into the bladder. See Ben-Meir D, McMullin N, Kimber C, Gibikote S, Kongola K, Hutson J M. "Reimplantation of obstructive megaureters with and without tailoring." J. Pediatr. Urol. 2006; 2: 178-81, incorporated herein by reference in its entirety. Ureteral reimplantation into the thickened trabeculated non-compliant bladder with friable mucosa imposes technical difficulty and increases the risk of postoperative ureteral stricture. See Brereton R J, Narayanan R, Ratnatunga C. "Ureteric re-implantation in the neuropathic bladder." Br. J. Surg. 1987; 74: 1107-10, incorporated hereinby reference in its entirety. Tailoring of megaureters might be complicated by stenosis at the ureterovesical anastomosis when excisional tapering is carried out, or excessive bulk of tissue when plicated. See Pantuck A J, Han K R, Perrotti M, Weiss R E, Cummings K B. "Ureteroenteric anastomosis in continent urinary diversion: long-term results and complications of direct versus nonrefluxing techniques." J. Urol. 2000; 163: 450-5, incorporated hereinby reference in its entirety. Likewise, ureterointestinal anastomosis using a nonrefluxing technique could result in higher rates of anastomotic stricture than the direct anastomosis.

In 1989, Studer et al. reported their first three years of experience of orthotopic ileal neobladder replacement, with an ileal loop chimney for direct ureteroileal anastomosis to prevent vesicoureteral reflux. See Studer U E, Ackermann D, Casanova G A, Zingg E J. "Three years' experience with an ileal low pressure bladder substitute." Br. J. Urol. 1989; 63: 43-52.8, incorporated hereinby reference in its entirety. The more recent study by Studer et. al. reporting on orthotopic neobladder in 482 patients with 20 years of experience showed the durable efficacy of using the ileal loop chimney for direct ureteroileal anastomosis with less than a 3% anastomotic stricture rate. Presently, based on a literature search, Studer's technique was described primarily for orthotopic neobladder replacement of the urinary bladder after cystectomy. See Studer U E, Burkhard F C, Schumacher M, Kessler T M, Thoeny H, Fleischmann A, Thalmann G N. "Twenty years experience with an ileal orthotopic low pressure bladder substitute-lessons to be learned." J. Urol. 2006; 176: 161-6, incorporated herein by reference in its entirety.

Though there are many well-documented methods of ileocystoplasty, difficulties remain for patients that suffer refractory neurogenic or nonneurogenic poorly-compliant bladders and concomitantly obstructed megaureters. While the goal is to retain efficacy and safety of any gastrointestinal procedure in the domains of bladder function, ureteral obstruction, renal functions, vesicoureteral reflux (VUR), febrile urinary tract infections (UTI), continence and complications.

In view of the forgoing, one objective of the present invention is to provide a procedure of augmentation cystoplasty employing a tissue flap that may be configured from afferent isoperistaltic tubularizedileal loop for direct ureteroileal anastomosis or a biologically compatible tissue flap generated in vitro then implanted. A further objective of the present disclosure is to provide a biologically compatible tissue flap that is configured to be implanted into a patient.

BRIEF SUMMARY OF THE INVENTION

According to a first aspect a method of augmenting a bladder including incising a native bladder along a sagittal plane between openings of two ureters in the native bladder to form an incised native bladder, implanting a tissue flap, comprising a bladder-expansion portion connected to a tubular portion, and suturing the bladder-expansion portion to an edge of the incised native bladder, wherein the method forms an augmented bladder with a volume capacity that is 100%-250% larger than a volume capacity of the native bladder.

In some implementations, the method further includes detaching the two ureters from the native bladder after incising the native bladder and before implanting the tissue flap.

In some implementations, the method further includes trimming a ureteral stenotic segment of each ureter to form a non-tailored end of each ureter.

In some implementations, the method further includes anastomosing a distal end of the tubular portion of the tissue flap to the non-tailored end of each ureter.

In some implementations of the method, the tissue flap is a biologically compatible tissue flap or a modified ileal segment.

In some implementations of the method, the tissue flap is the modified ileal segment and the method further includes isolating a native ileal segment such that a segmental blood supply of the native ileal segment is retained and the native ileal segment has two ends, cutting a segment of an antimesenteric border of the native ileal segment to form a cut ileal segment with a detubularized first end with two cut edges, and a second end that forms the tubular portion of the tissue flap, and attaching a part of the length of one cut edge of the detubularized first end to the cut ileal segment to form the bladder-expansion portion of the tissue flap.

In some implementations of the method, the native ileal segment is of length 20 cm-45 cm and a distance of at least 10 cm from an ileocecal valve.

In some implementations of the method, the segment of the antimesenteric border of the native ileal segment is 5 cm-8 cm in length.

In some implementations of the method, the tissue flap is the biologically compatible tissue flap, which is grown on a biocompatible scaffold.

In some implementations of the method, the biocompatible scaffold comprises a collagen mesh.

In some implementations of the method, the collagen mesh is coated by a biochemical factor, a cell derived matrix, and/or a synthetic biocompatible polymer, and bladder cells.

In some implementations of the method, the collagen mesh is coated by the biochemical factor, which is selected from the group consisting of a growth hormone, a steroid, an immunomodulatory, a growth inhibitor, an antibiotic, a nutrient, an amino acid, and a protein.

In some implementations of the method, the collagen mesh is coated by the cell derived matrix, which is a progenitor cell, a stem cell, a bladder submucosa, an alginate, and/or small-intestinal submucosa.

In some implementations of the method, the collagen mesh is coated by the synthetic biocompatible polymer, which is a polyglycolic acid, a polylactic acid, and/or a poly(lactic-co-glycolic acid).

In some implementations of the method, the bladder-expansion portion is a curved structure having a lumen-exposed surface, which faces an interior of the augmented bladder, and a peritoneum-exposed surface, which faces an exterior of the augmented bladder.

In some implementations of the method, the tubular portion of the biologically compatible tissue flap is a hollow cylindrical shape, having an interior radius of 5 mm-10 mm, an interior surface comprising the lumen-exposed surface, which is continuous with the lumen-exposed surface of the bladder-expansion portion, and an exterior surface having the peritoneum-exposed surface, which is continuous with the peritoneum-exposed surface of the bladder-expansion portion.

In some implementations of the method, the lumen-exposed surface of the bladder-expansion portion has a surface area of 25 cm$^2$-45 cm$^2$ and the lumen-exposed surface of the interior surface of the tubular portion is 5 cm$^2$-15 cm$^2$.

In some implementations of the method, the bladder expansion portion is sutured to the edge of the incised native bladder with absorbable sutures.

According to a second aspect a biologically compatible tissue flap for augmenting a native bladder including a biocompatible scaffold comprising a collagen mesh that coated by at least one biochemical factor, selected from the group consisting of a growth hormone, a steroid, an immunomodulatory, a growth inhibitor, an antibiotic, a nutrient, an amino acid, and/or a protein; at least one cell derived matrix selected from the group consisting of a progenitor cell, a stem cell, a bladder submucosa, an alginate, small-intestinal submucosa; and at least one synthetic biocompatible polymer, selected from the group consisting of a polyglycolic acid, a polylactic acid, and/or a poly(lactic-co-glycolic acid, and/or bladder cells. The biocompatible scaffold is configured with a bladder-expansion portion and a tubular portion that is sutured to an incised native bladder to form an augmented bladder.

In some implementations of the method, the bladder-expansion portion is a curved structure having a lumen-exposed surface that faces an interior of the augmented bladder, and a peritoneum-exposed surface that faces an exterior of the augmented bladder; and the tubular portion has an interior radius of 5 mm-10 mm, an interior surface having the lumen-exposed surface, and an exterior surface comprising the peritoneum-exposed surface.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
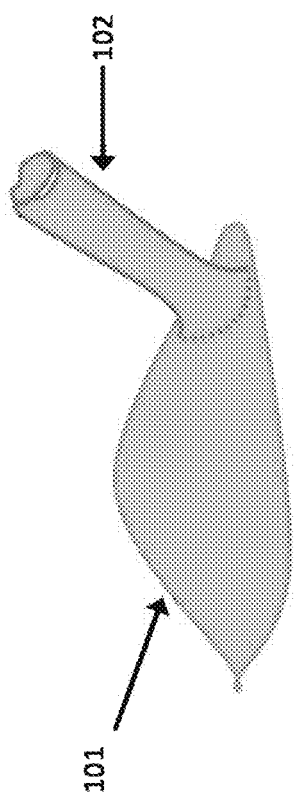
FIG. 1 is a schematic of the tissue flap that may be formed by a modified ileal segment or the biologically compatible tissue flap.

Throughout the specification ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "biocompatible" refers to a substance that is substantially non-toxic to a subject. When "biocompatible" is used in reference to a biologically compatible tissue flap, as described herein, "biocompatible" refers to an artificial or exogenous tissue flap that is implanted into a patient and is non-toxic to that patient.

"Biodegradable" is generally referred to herein as a material that will erode to soluble species or that will degrade under physiologic conditions to smaller units or chemical species that are, themselves, non-toxic (biocompatible) to the subject and capable of being metabolized, eliminated, or excreted by the subject.

A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. Bioactive agents also include those substances which affect the structure or function of a subject, or a pro-drug, which becomes bioactive or more bioactive after it has been placed in a predetermined physiological environment.

Referring now to the drawings, wherein like reference numerals designate identical or corresponding parts throughout the several views.

An aspect of the present disclosure relates to a method of augmenting a bladder. The method includes incising a native bladder along a sagittal plane between openings of two ureters in the native bladder to form an incised native bladder. The native bladder is a bladder organ in a subject. Incising the native bladder may include a cut made through an outer tissue of the native bladder to facilitate an augmentation as described by the present disclosure. Incising of the native bladder leaves behind an edge consisting of tissue, leaving an opening of the native bladder forming the incised native bladder or "wide-opened native bladder". The outer tissue may include a peritoneum and tissue of the native bladder. Cutting may be accomplished by a metal scalpel, laser scalpel, soft-tissue laser, or other cutting tools known to those familiar with surgical arts. In general, a surgical incision is made as small and unobtrusive as possible to facilitate safe and timely operating conditions. Once the incision is made, a tissue flap may be implanted. The tissue flap may be described as having a bladder-expansion portion connected to a tubular portion. FIG. 1 depicts a schematic representation of the tissue flap 100, the bladder expansion portion 101, and the tubular portion 102. During the implanting, tools such as clamps and clips may be employed to hold the tissue flap in place. Upon implanting the tissue flap, the bladder-expansion portion is sutured to the edge of the incised native bladder. Clamps and clips may be removed once suturing is completed. The method forms an augmented bladder with a volume capacity that is larger than a volume capacity of the native bladder by about 100%-250%, about 110%-240%, about 120%-230%, about 140%-220%, about 150%-210%, about 160%-200%, or about 170%-190%.

In some implementations, the method further includes detaching the two ureters from the native bladder after incising the native bladder and before implanting the tissue flap. Some ureters are often twisted and thus detaching them allows for correcting any twists in the ureter. The ureters are detached from the bladder by cutting methods as described herein. Furthermore, in some implementations, after the ureters are detached from the native bladder, trimming a ureteral stenotic segment of each ureter may follow to form a non-tailored end of each ureter. The ureteral stenotic segment may be constricted which may cause complications for the subject undergoing the method of the present disclosure and therefore may be trimmed by about 1 cm-5 cm, about 1.5 cm-4 cm, about 1.75 cm-3 cm, or about 2 cm-2.5 cm. In some implementations, the method further includes anastomosing a distal end of the tubular portion 102 of the tissue flap to the non-tailored end of each ureter. Anastomosing is the connection of two structures, such as two tubular structures. Anastomosing may include suturing with biodegradable suture thread, biodegradable staples, or a biodegradable adhesive, all of which may be absorbed by a body tissue as healing progresses by the growth of new cells. The biodegradable suture thread, the biodegradable staples, or the biodegradable ahesives are commonly comprised of natural collagen, polyglycolic acid polyester, and poly (p-dioxanone). One ureter and the tubular portion 102 of the tissue flap may be anastomosed end-to-end, while the second ureter may be connected end-to-side of the tubular portion 102 of the tissue flap. Alternatively, both ureters may be anastomosed to the distal end of the tubular portion 102.

Figure 2B:
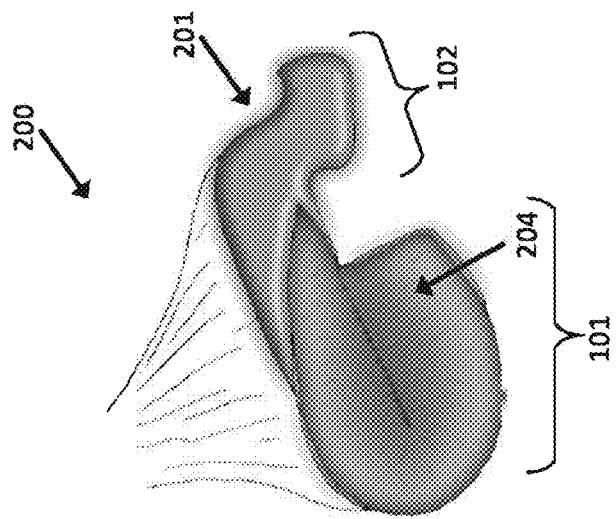
FIG. 2B is a drawing of an ileal segment undergoing modification and depicts the bladder-expansion portion of the tissue flap.
Figure 2A:
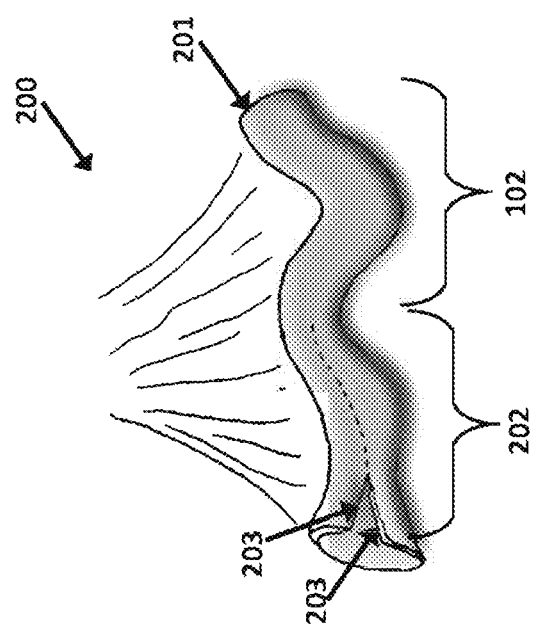
FIG. 2A is a drawing of an ileal segment undergoing modification.
Figure 3A:
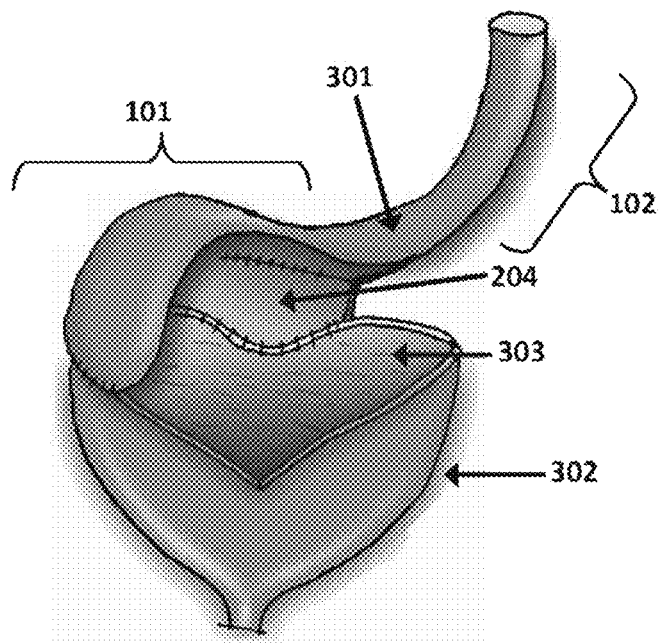
FIG. 3A is a drawing of a bladder undergoing augmentation by suturing the tissue flap to the incised native bladder.
Figure 3B:
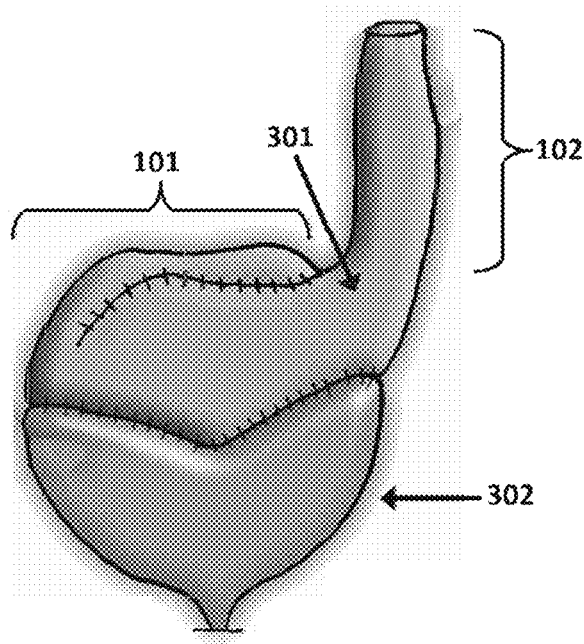
FIG. 3B is a drawing of the augmented bladder.

In some implementations of the method, the tissue flap is a modified ileal segment. To obtain and prepare the modified ileal segment, the method may further include isolating a native ileal segment such that a segmental blood supply of the native ileal segment is retained. In some implementations of the method, the native ileal segment is of length about 20 cm-45 cm, about 22 cm-42 cm, about 24 cm-40 cm, or about 26 cm-38 cm. The native ileal segment may be a distance of at least 10 cm, at least 12 cm, at least 15 cm at least 18 cm, or at most 20 cm from an ileocecal valve. FIG. 2A and FIG. 2B depict the native ileal segment 200 undergoing modification. The isolating will result in the native ileal segment 201 having two ends. A segment of the native ileal segment is cut along an antimesenteric border of the native ileal segment to form a cut ileal segment with a detubularized first end 202 with two cut edges 203, and a second end that forms the tubular portion 102 of the tissue flap 100. The segment may be about 5 cm-8 cm in length, about 5.5 cm-7.5 cm in length, or about 6 cm-7 cm in length. To form the bladder-expansion portion 101 of the tissue flap with the native ileal segment, one of the two cut edges 203 is turned in on itself and reattached by suturing as described herein. The second end of the native ileal segment remains tubular in shape and attached to the first end, and the second end is anastomosed to the ureters as described herein. The cut edges may be a length of about 3 cm-8 cm, about 4 cm-7 cm. or about 5 cm-6 cm. FIG. 2B depicts the modified ileal segment. Upon attaching one of the two cut edges 203 to form the bladder-expansion portion 101 of the tissue flap 100, the tubular portion 102 remains attached to the bladder-expansion portion and now comprises an interior and an exterior. FIG. 3A and FIG. 3B depict a schematic of the incised native bladder undergoing augmentation by attaching the modified ileal segment. The interior 204 of the modified ileal segment may be facing the inside 303 of the incised native bladder 302 once sutured to the incised native bladder opening with biodegradable or absorbable sutures.

In some implementations, the interior 204 may be a lumen-exposed surface and the exterior may be a peritoneum-exposed surface 301. A lumen is an interior of organs and tubular structure in anatomy, such as a lumen of a bladder is a space 303 where urine is contained. A peritoneum is composed of a layer of mesothelium (a thin skin-like tissue) supported by a thin layer of connective tissue (e.g. collagen). The peritoneum covers most of the intraabdominal organs and supports the abdominal organs and serves as a conduit for blood vessels, lymph vessels, and nerves in a human body. The lumen-exposed surface of the bladder-expansion portion may have a surface area of about 25 cm$^2$-45 cm$^2$, about 27 cm$^2$-42 cm$^2$, about 30 cm$^2$-40 cm$^2$, about 32 cm$^2$-38 cm$^2$, or about 34 cm$^2$-36 cm$^2$.

In some implementations, the tubular portion 102 of the tissue flap has an interior surface comprising the lumen-exposed surface 204, which is continuous with the lumen-exposed surface of the bladder-expansion portion, and an exterior surface having the peritoneum-exposed surface 301, which is continuous with the peritoneum-exposed surface of the bladder-expansion portion 101. The lumen-exposed surface of the interior surface of the tubular portion 102 may be about 5 cm$^2$-15 cm$^2$, about 6 cm$^2$-14 cm$^2$, about 7 cm$^2$-13 cm$^2$, about 8 cm$^2$-12 cm$^2$, or about 9 cm$^2$-11 cm.

In some implementations of the method, the bladder expansion portion is sutured to the edge of the incised native bladder 302 with absorbable sutures, or sutures as described herein to form the augmented bladder.

In some implementations of the method, the bladder-expansion portion is a curved structure having a lumen-exposed surface 204, which faces an interior of the augmented bladder, and a peritoneum-exposed surface 301, which faces an exterior of the augmented bladder.

In some implementations of the method of the present disclosure, the tissue flap 100 as described herein may be a biologically compatible tissue flap, which is grown on a biocompatible scaffold. The biologically compatible tissue flap is an artificial implant that is prepared in a laboratory and implanted into a subject undergoing a bladder augmentation procedure. The biocompatible scaffold may comprise several layers. The biocompatible scaffold may include a central layer to provide structure and a degree of rigidity and an intermediate layer which extends outward from the central layer. Some intermediate layers may include a growth surface comprising various growth factors and extracellular matrix mimicking molecules. The biocompatible scaffold may have an external layer of cells that are sustained and proliferated in culture prior to implantation of the biocompatible scaffold.

In some implementations, the biocompatible scaffold comprises a collagen mesh. Collagen is the most abundant fibrous structural protein found in mammals and has been shown to exhibit many desirable qualities in scaffolding materials. For example, in addition to good bioaffinity, or a propensity to be compatible with another biological molecule, and histocompatibility, or a property of having a similar or compatible antigen, wound healing cells such as fibroblasts have been shown to have good affinity for collagen, and the presence of collagen in the biocompatible scaffold can encourage and promote cell growth and differentiation of the tissues/cells associated with the biocompatible scaffold. In addition, collagen can act as a conduit for healthy cells and nutrients from surrounding healthy tissue, such as healthy bladder tissue, to a suture site. The collagen mesh may include any collagen type or combination of collagen types. For instance, a collagen mesh can include any one or combination of the currently known 28 types of collagen. Typically, a collagen mesh can include at least some type I and/or type II collagen, as types I and II collagen are the most abundant types of collagen, and the introduction of organized type I collagen has been shown to be beneficial in cellular integration. The presence of either collagen type is not a requirement in a collagen mesh as disclosed herein.

A collagen mesh may be derived of any suitable collagen source and formed according to any suitable method as is understood by one of ordinary skill in the art. For example, a collagen-based scaffold can include natural collagen-containing tissues that can be allograft, autograft, and/or xenograft tissues. Natural collagen-containing tissues that can be used to form a scaffold can include, without limitation, soft tissues including ligament, tendon, muscle, dura, pericardium, fascia, peritoneum, and the like and can be derived from any host source (human, equine, porcine, bovine, etc.).

Moreover, the collagen mesh may further include non-collagen polymers or polymer-like materials. For instance, in one embodiment, a mesh can include a non-collagen hydrogel matrix. Hydrogel scaffolds are known in the art and are generally defined to include polymeric matrices that can be highly hydrated while maintaining structural stability. Suitable hydrogel mesh can include non-crosslinked and crosslinked hydrogels. In addition, crosslinked hydrogel mesh can optionally include hydrolyzable portions, such that the mesh can be degradable when utilized in an aqueous environment. For example, in one embodiment, the collagen mesh may include a cross-linked hydrogel including a hydrolyzable cross-linking agent, such as polylactic acid, and can be degradable in an aqueous environment.

Hydrogel mesh may include natural polymers such as glycosaminoglycans, polysaccharides, proteins, and the like, as well as synthetic polymers, as are generally known in the art. A non-limiting list of polymeric materials that can be utilized in forming hydrogel mesh, in addition to collagen, previously discussed, can include dextran, hyaluronic acid, chitin, heparin, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

Hydrogel mesh may be formed according to any method as is generally known in the art. For instance, a hydrogel can self-assemble upon mere contact of the various components or upon contact in conjunction with the presence of particular external conditions (such as temperature or pH). Alternatively, assembly can be induced according to any known method following mixing of the components. For example, step-wise or chain polymerization of multifunctional monomers or macromers can be induced via photopolymerization, temperature dependent polymerization, and/or chemically activated polymerization. Optionally, a hydrogel can be polymerized in the presence of an initiator. For example, in one embodiment, a hydrogel mesh can be photopolymerized in the presence of a suitable initiator such as Irgacuree or Darocur® photoinitiators available from Ciba Specialty Chemicals. In another embodiment, a cationic initiator can be present. For example, a polyvalent elemental cation such as $Ca^{2+}$, $Mg^{2+}$, $Al^{3+}$, $La^{3+}$, or $Mn^{2+}$ can be used. In another embodiment, a polycationic polypeptide such as polylysine or polyarginine can be utilized as an initiator.

The collagen mesh may comprise hydrogel in the amount of about 5%-99%, about 10%-95%, about 15%-90%, about 20%-85%, about 25%-80%, about 30%-75%, about 35%-70%, about 40%-65%, about 45%-60%, or about 50%-55%, relative to a total collagen mesh composition.

In some implementations of the method, the collagen mesh may by coated by a biochemical factor, a cell derived matrix, a synthetic biocompatible polymer, and bladder cells.

Biochemical factors are well known in the art. The biochemical factor may include, but is not limited to a growth hormone, a steroid, an immunomodulator, a growth inhibitor, an antibiotic, a nutrient, an amino acid, and a protein. For example, the growth hormone or growth inhibitor may include, but is not limited to growth factors, such as Insulin-like growth factor-I (IGF-I), IGF-II, Transforming growth factor-β (TGF-β) I-III, vascular endothelial growth factors, fibroblast growth factors, platelet derived growth factors, insulin derived growth factor, or transforming growth factors, parathyroid hormone, parathyroid hormone related peptide, TGFβ superfamily factors, sonic hedgehog, growth differentiation factor-5 (GDF-5); GDF6; GDF8; or PDGF. For example, the immunomodulatory may include, but is not limited to interleukins, such as IL-2, IL-7, IL-12, cytokines, or interferons, such as G-CSF. For example, the steroid may include such as glucocorticoids, cortisol, or derivatives thereof. The antibiotic may include, but is not limited to a β-lactamase inhibitor, a cephalosporin, chloramphenicol, clindamycin, fusidic acid, a glycopeptide, a macrolide, metronidazole, mupirocin, a penicillin, a polyene, a quinolone, a rifamycin, a sufonamide, a tetracyclines exemplified by doxycycline, minocycline, tigecycline, trimethoprim, and combinations thereof. For example, the nutrient may include, but is not limited to carbohydrates, fats, or minerals, such as calcium, manganese, selenium, magnesium, or zinc. The amino acid may include individual amino acids or polymeric amino acids. The protein may include, but is not limited to elastin, fibronectin, laminin, proteases, or pro-enzymes. In some embodiments, a bioactive agent may be described as a biochemical factor and may further coat the collagen mesh. The biochemical factor may coat a percentage of a total surface area of the collagen mesh. For example, the percentage may be about 1%-60%, about 2%-55%, about 4%-50%, about 6%-45%, about 8%-40%, about 10%-35%, about 15%-25%, or about 20%-22%.

The cell derived matrixis well known in the art and may include, but is not limited to a progenitor cell, a stem cell, a bladder submucosa, an alginate, and/or small-intestinal submucosa. Cell-derived matrices are extracellular matrices that are a product of matrix secretion and assembly by cells cultured at high density in vitro. After the removal of the cells that produced the matrix, an assembled matrix scaffold is left that closely mimics native stromal fiber organization and molecular content, which can be used to promote further cell growth if applied to a different surface. Cell-derived matrices have been shown to impart in vivo-like responses to cells cultured in these matrices, such as progenitor cells, stem cells, or various organ tissue cells. The progenitor cell is a biological cell that, like a stem cell, has a tendency to differentiate into a specific type of cell, but is already more specific than a stem cell and is pushed to differentiate into its "target" cell. For example, the progenitor cell may be a mucosa cell, a submucosa cell, a muscular propria cell, or a adventitia cell. Similarly, the stem cell may also differentiate into various bladder cell types or small intestine cell-types, such as the small-intestine submucosa. The cell derived matrix may coat a percentage of a total surface area of the collagen mesh. For example, the percentage may be about 1%-90%, about 5%-85%, about 10%-80%, about 15%-75%, about 20%-70%, about 25%-75%, about 30%-70%, about 35%-65%, about 40%-60%, or about 45%-55%.

In some implementations of the method, the collagen mesh is coated by the synthetic biocompatible polymer. Synthetic biocompatible polymers are well known in the art and may include, but is not limited to a polyglycolic acid, a polylactic acid, and/or a poly(lactic-co-glycolic acid). In some implementations, the synthetic biocompatible polymers may be integrally incorporated with the collagen mesh.

The collagen mesh described above, may be shaped as a curved structure having a lumen-exposed surface, which faces an interior of the augmented bladder, and a peritoneum-exposed surface, which faces an exterior of the augmented bladder. Upon coating the collagen mesh with various biochemical factors, the cell derived matrix, and/or the synthetic biocompatible polymer, and bladder cells, the lumen-exposed surface will comprise the bladder cells that mimic the native bladder interior-facing surface and the peritoneum-exposed surface will mimic the native bladder exterior-facing surface. The biologically compatible tissue flap may be partially prepared in a lab under conditions known to those familiar in the art. For example, the biologically compatible tissue flap may be prepared with the collagen mesh and coated with the various materials described herein and cultured in a $CO_2$ incubator at 32° C., with appropriate sterile conditions and nutrients added to stimulate proliferation of cells coating the collagen mesh.

In some embodiments, the tubular portion of the biologically compatible tissue flap is a hollow cylindrical shape, having an interior radius of about 5 mm-10 mm, about 6 mm-9 mm, or about 7 mm-8 mm. The tubular portion of the biologically compatible tissue flap may have an interior surface comprising the lumen-exposed surface, which is continuous with the lumen-exposed surface of the bladder-expansion portion, and an exterior surface having the peritoneum-exposed surface, which is continuous with the peritoneum-exposed surface of the bladder-expansion portion. The lumen-exposed surface and the peritoneum-exposed surface will mimic the bladder cells in the respective orientation as described herein.

In some embodiments, the lumen-exposed surface of the bladder-expansion portion of the biologically compatible tissue flap may have a surface area of about 25 $cm^2$-45 $cm^2$, about 27 $cm^2$-42 $cm^2$, about 30 $cm^2$-40 $cm^2$, about 32 $cm^2$-38 $cm^2$, or about 34 $cm^2$-36 $cm^2$. In some embodiments, the lumen-exposed surface of the interior surface of the tubular portion of the biologically compatible tissue flap may be about 5 $cm^2$-15 $cm^2$, about 6 $cm^2$-14 $cm^2$, about 7 $cm^2$-13 $cm^2$, about 8 $cm^2$-12 $cm^2$, or about 9 $cm^2$-11 cm.

In some implementations of the method, the bladder expansion portion of the biologically compatible tissue flap may be sutured to the edge of the incised native bladder with absorbable sutures, as described herein. Either the modified ileal segment of the biologically compatible tissue flap may be implanted on to the incised native bladder to form the augmented bladder.

In some implementations, the method may increase bladder compliance by about 100%-1000%, about 150%-950%, about 200%-900%, about 250%-850%, about 300%-800%, about 350%-750%, about 400%-700%, or about 550%-650%. In some implementations, the method may reduce ureteral diameter by 0.1%-90%, about 0.5%-85%, about 1%-80%, about 5%-75%, about 7%-70%, about 10%-65%, about 15%-60%, about 20%-55%, about 25%-50%, about 30%-45%, or about 35%-40%.

A further aspect of the present disclosure relates to a biologically compatible tissue flap for augmenting a native bladder comprising elements as described herein.

The examples below are intended to further illustrate augmentation of a native bladder and are not intended to limit the scope of the claims.

EXAMPLE

Methods
Setting

We carried out an ethics committee-approved retrospective review and analysis of data of 21 children who underwent the fez procedure at King Abdulaziz University Hospital, Jeddah, Saudi Arabia, between March 2004 and June 2011.

Inclusion/Previous Management and Exclusion Criteria

The children had been previously presented during their early lives with neurogenic bladder as a result of myelodysplasia (17 children), or posterior urethral valve bladder (four children). All children were incontinent to urine, whereas 15 patients had recurrent febrile UTIs. Six patients showed grade 4-5VUR at their initial VCUG. The children were initially refractory to anticholinergics, botulinum toxin-A intravesical injections, CIC and/or antibiotics suppression; with progressive decline of renal functions. Ureteral obstruction was suspected from ultrasonography and 99mTc-DTPA diuretic renography with evidence of hydroureteronephrosis and prolonged T1/2. Ureteral obstruction was further proved by failure of renal function to respond to an initial 2 to 4-week period of urethral catheterization; followed by improvement of renal function and elimination of obstruction at 99mTc-DTPA diuretic renography after an additional 2 to 4-week period of nephrostomy catheterization. Patients with documented ureteral obstruction (18 bilateral and three unilateral; total 39 megaureters) were further managed with cutaneous ureterostomies, or continued on the nephrostomies, awaiting their growth. At the time of fez surgery, 17 children had preliminary cutaneous ureterostomies, whereas four children were on temporary nephrostomies. The mean age at ureterostomy(ies) was 2.5 years (range 7 months to 4 years), and the children underwent the fez procedure after 3-9 years after ureterostomy(ies). Patients who responded favorably to the initial 2-4 weeks of urethral catheterization were offered other alternatives (e.g. anticholinergics and CIC, or vesicostomy), and were not included in the current study. Children with glomerular filtration rate (GFR)<30 mL/min or serum creatinine>2 mg/d were not offered the fez surgery for bladder augmentation.

Fez Procedure (Bladder Augmentation)

Figure 4:
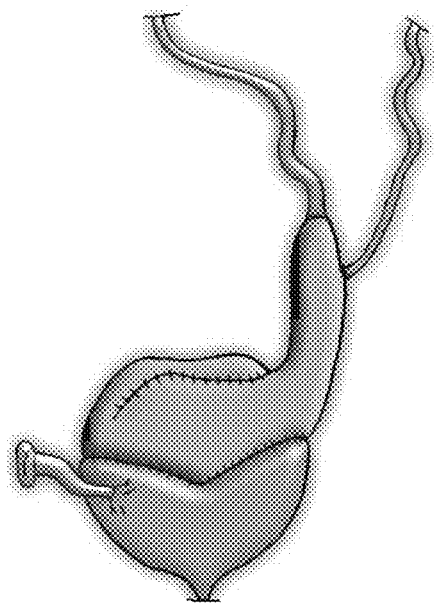
FIG. 4 is a drawing of the augmented bladder with ureters attached.
Figure 5:
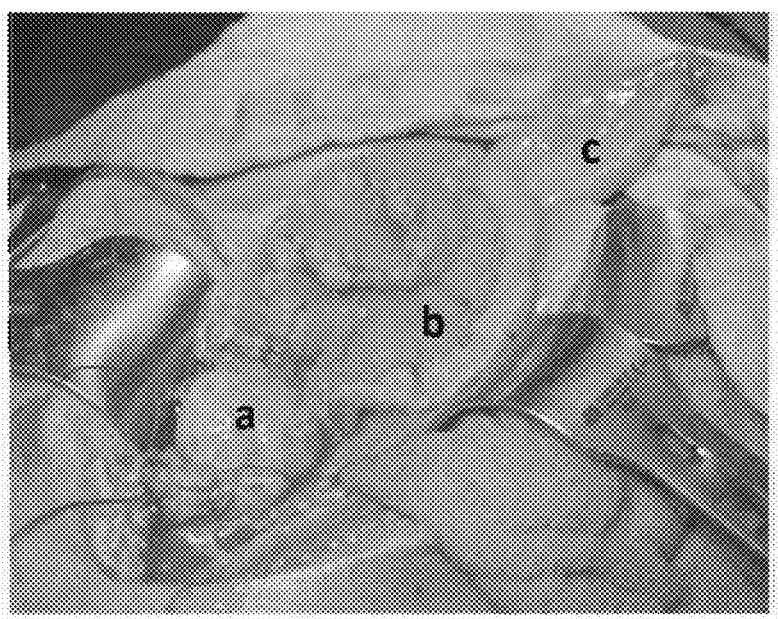
FIG. 5 is a photograph of the surgical site of a subject who has undergone the bladder modification.

The native bladder was widely incised sagittally down to the level of the interureteric ridge. The ureter(s) were dissected, tortuosities were corrected, and the ureteral stenotic segment and extra length were trimmed. As a modification of Studer's procedure, a 25 to 40-cm ileal segment 200, at least 15 cm from the ileocecal valve, was isolated with its segmental blood supply, and the ileal continuity was reestablished. The selected segment was detubularized by opening its antimesenteric border, keeping the proximal 5 cm of the segment as an afferent isoperistaltic tubularized loop 102. The detubularized segment 202 was constructed as a U- or W-shaped patch (FIG. 2B). The ileal patch (i.e. the modified ileal segment) was sutured with absorbable sutures to the wide-opened native bladder 302 to prevent the hourglass deformity, and to configure the bladder in a spherical shape (FIG. 3A and FIG. 3B). The ileal patch with its tubularized loop 102, when sutured to the bladder, was finally fashioned as a "fez" with its tassel (FIG. 3B). The tubularized loop was directly anastomosed to the non-tailored ureter(s) (FIG. 4); as end-to-end with the right ureter and end-to-side with the left ureter in bilateral megaureters, or end-to-end in unilateral disease (FIG. 4 and FIG. 5). The ureteroileal anastomoses were stented, a suprapubic catheter was brought out of the native bladder and perivesical drains were secured. A concomitant Mitrofanoff catheterizable channel using the appendix was carried out in 16 patients to facilitate CIC. No concomitant bladder neck surgery was carried out in the reported patients. Ureteral stents were removed after 2-3 weeks, whereas cystography was carried out 4 weeks after surgery, and the suprapubic catheters were removed if there was no extravasation.

Follow Up

Visits after fez surgery were typically scheduled at 3-month intervals for the first year; and every 6 months thereafter. Urine analysis, urine culture/sensitivity tests, serum creatinine and ultrasonography of kidney-ureter-bladder were carried out at each visit; whereas voiding cystourethrogram (VCUG) was carried out at the first 3-month visit. 99mTc-Diethylenetriamine pentaacetate (DTPA) diuretic renography and urodynamic cystometry studies were carried out every 6 months for the first 2 years, and were then repeated annually. The measured outcomes were changes in cystometric capacity and bladder compliance, degree of hydroureteronephrosis in ultrasonography, 99mTc-DTPA evidence of ureteral obstruction (T1/2), 99mTc-DTPA determined GFR, serum creatinine, documentation of reflux on VCUG and febrile UTIs episodes. Improvements of urinary incontinence, documented complications after surgery and length of hospital stay were also analyzed. Statistical analysis: The Wilcoxon signed-rank test was carried out using GraphPad InStat version 3.06 for Windows (GraphPad Software, San Diego, Calif., USA). Two-tailed P<0.05 was considered significant.

Results

The present study included 21 children, 15 boys and six girls, with a mean age of 9.4±1.3 years (range 6-12 years) at the time of fez surgery. The mean operative time was 301±40 min (range 250-370 min).

TABLE 1

Pre- and post-fez surgery studies of bladder and renal functions.

|  | Pre-op mean ± SD (range) | Post-op mean ± SD (range) | Change mean ± SD (95% CI of change) | % Change | P |
|---|---|---|---|---|---|
| Cystometric capacity (mL)† | 96.9 ± 21.4 (62-135) | 370.1 ± 79.2 (221-458) | 273.2 ± 60.9 (245.5 to 301) | 282% | 0.0001 |
| Bladder compliance (mL/cm H$_2$O)† | 3.1 ± 1.2 (1.1-5.2) | 18.7 ± 5.2 (10.2-31.4) | 15.6 ± 4.2 (13.6 to 17.5) | 503% | 0.0001 |
| GFR (mL/min)† | 62.0 ± 10.7 (45-77) | 60.2 ± 11.5 (43-80) | −1.81 ± 5.1 (−1.14 to 0.52) | −2.9% | 0.22 |
| Serum creatinine (mg/dL)† | 1.05 ± 0.4 (0.4-1.7) | 1.16 ± 0.43 (0.42-1.84) | 0.1 ± 0.27 (−0.01 to 0.23) | 9.5% | 0.18 |
| T½ (min)‡ | 27 ± 5.03 (24-41) | 12.9 ± 2.4 (9-18) | −14.1 ± 5.7 (−16 to 12.3) | −52.2% | 0.0001 |
| Ureteral diameter (mm)‡ | 13.3 ± 4.8 (8-25) | 6.1 ± 2.1 (5-14) | −7.26 ± 3.6 (−8.4 to −6.1) | −54.4% | 0.0001 |

†Assessment before fez versus the latest post-fez follow-up.
‡initial assessment (before nephrostomy:ureterostomy) versus latest post-fez follow-up.

The postoperative hospital stay varied between 15 and 33 days with a mean of 23.3±5.8 days. The follow-up period after fez surgery ranged between 18 and 78 months, with a mean of 52.5±12.8 months. The mean±SD of preoperative cystometric capacity (96.9±21.4 ml) and bladder compliance (3.1±1.2 ml/cm $H_2O$) showed significant improvements during follow up (P<0.0001, each). After the fez surgery, the cystometric capacity mean change±SD was 273.2±60.9 ml (95% CI 245.5-301); whereas the bladder compliance mean change was 15.6±4.2 mL/cm $H_2O$ (95% CI 13.6-17.5); with a percentage change of 282% and 503%, respectively (Table 1). Improvement of hydroureteronephrosis was evident on ultrasonography of all patients; although none of them had complete resolution. Likewise, resolution of ureteral obstruction was documented at follow-up 99mTc-DTPA diuretic renography studies of all patients, and none of them experienced reobstruction of the ureters (Table 1). The improved renal function, previously documented with the preliminary cutaneous ureterostomies or nephrostomy catheters, were maintained after fez surgery (Table 1) with non-significant changes of the improved GFR (P=0.22) and serum creatinine (P=0.18). Continence between CIC was observed in all patients; although two patients required anticholinergics to achieve continence. None of the patients showed VUR after fez surgery, and febrile UTIs episodes were also resolved in all children. No significant intraoperative or postoperative complications, such as significant bleeding necessitating blood transfusion, wound dehiscence, sepsis or anastomosis leaks, were reported. However, Mitrofanoff stomal stenosis was seen in one patient and was successfully revised.

Discussion

Augmentation cystoplasty has been advocated as a sufficient procedure to resolve refluxing megaureters in neurogenic bladder, with no necessity to carry out ureteral reimplantation. However, in obstructed megaureters, the decision of surgical intervention is more complex. As long as renal functions are not significantly jeopardized and UTIs are not a major concern, the basic management is antibiotic suppression with close observation, and no surgery should be carried out. If surgery is warranted, repair is typically carried out between 1 and 2 years-of-age, as earlier surgical intervention is fraught with higher complication rates. Surgery usually entails reimplanting the plicated or tapered ureter into the bladder. Plication usually results in a bulky ureter, whereas tapering can lead to anastomotic stricture. Furthermore, the thick non-pliable bladder might encumber the reimplantation of the ureter, and increases the risk of postoperative ureteral stricture. Nevertheless, different procedures were described to implant the ureters into bowel segments used for orthotopic neobladders; including both antireflux and direct anastomosis procedures. The benefits of antireflux techniques have been overestimated despite the higher rates of stricture formation; and direct ureteroileal anastomosis seems to be more rational than antireflux techniques for non-dilated ureters. Hassan et al. compared the outcomes of the Le Ducantireflux technique versus direct anastomosis for ureteral implantation in the setting of orthotopic Y-ileal neobladder. Unilateral ureteroileal anastomotic stricture was encountered in 9.7% of Le Duc patients compared with none of the direct anastomosis patients. Additionally, antirefluxing techniques did not guarantee the non-existence of reflux, particularly with preoperatively dilated ureters.13 Similarly, Shigemura compared the direct ureteroileal anastomosis using the Wallace method versus Le Duc ureteroileal anastomosis in modified Studer's orthotopic neobladder reconstruction, and they concluded that direct ureteroileal anastomosis was a simple technique minimizing the incidence of anastomotic stenosis. Furthermore, Waidelich et al. reported on 15 patients with direct ureteroileal anastomosis using Studer's technique, and confirmed the postoperative absence of vesicoureteral reflux.

The present series included a particularly complex group of 21 children who had presented in their early lives with refractory poorly-compliant bladders, of neurogenic or non-neurogenic origin and documented obstructed megaureters; with or without VUR. The patients were incontinent to urine, showed progressive deterioration of renal functions and 15 of them experienced repeated episodes of febrile UTIs. The patients were refractory to less invasive managements with anticholinergics, botulinum toxin-A intravesical injections, CIC and/or antibiotics suppression; thus necessitating the preliminary management of cutaneous ureterostomies in 17 patients and temporary nephrostomies in four patients. Fez surgery was applied to those children who showed improvements of renal function and resolution of obstruction after cutaneous ureterostomies or, alternatively, after the nephrostomies. Studer's procedure was basically designed as an ileal neobladder to replace the bladder after cystectomy procedures. We described the procedure using an ileal patch in continuity with an afferent isoperistaltic ileal loop for augmentation cystoplasty and direct ureteroileal anastomosis in this particular group of patients. The augmented bladder with its attached ileal loop, when distended, resembles the fez a traditional Arabic hat—with its attached tassel; hence, we named this technique the "fez procedure."

Augmentation ileocystoplasty in the patients resulted insignificant improvements of bladder function with a significant increase (P<0.0001) of both bladder capacity (282%) and bladder compliance (503%). Additionally, the application of this procedure resolved the ureteral obstruction in all children with no restenosis formation. Furthermore, none of the patients demonstrated reflux; showing the efficacy of this simplified direct ureteral anastomosis to the tubularized ileal loop in the prevention of reflux. The improvements of bladder functions and the resolution of ureteral obstruction consequently maintained preserving the renal function—an ultimate goal—with continued improvement of GFR and serum creatinine after fez surgery. The procedure was also effective in controlling febrile UTIs episodes and incontinence in all children; although two patients required anticholinergics to achieve continence.

The safety of the present procedure was observable, as none of the patients experienced significant intra- or postoperative complications; further highlighting the relative simplicity of this procedure. Stenosis of the Mitrofanoff stoma was seen in one patient, which required a secondary procedure and was successfully revised.

The presently described procedure is not described elsewhere. Additionally, although controversy exists on the necessity of ureteral reimplantation to eliminate VUR in refractory patients undergoing augmentation ileocystoplasty for noncompliant bladders and refluxing ureters, the present procedure might also be studied in such patients as a potential simplified antireflux measure with a minimal stricture rate. The fez procedure could also have a potential to be studied in other conditions associated with contracted bladder and concomitant ureteral strictures, such as tuberculosis or schistosomiasis.

The retrospective design, and the limited number of patients were limitations of the present study. Of note, ureteral dilatation in children with neurogenic bladder is usually secondary to increased intravesical pressure, and improving bladder compliance will consequently improve the ureteral dilatation in the majority. Thus, the procedure was proposed to manage an group of complex patients with evidence of refractory poorly-compliant bladders and proved concomitantly obstructed megaureters.

The fez procedure bladder augmentation, entailing augmentation ileocystoplasty and direct ureteral anastomosis to an afferent tubularized ileal loop, was applied to this particularly complex group of children with refractory poorly-compliant bladders and concomitantly obstructed megaureters. The procedure proved to be a versatile and successful surgical option, with improvements of bladder capacity/compliance, resolution of ureteral obstruction and VUR, preservation of renal functions, controlling symptomatic UTIs and incontinence, and showing acceptable morbidity.

The invention claimed is:

1. A method of augmenting a bladder of a subject comprising:
   incising a native bladder along a sagittal plane between openings of two ureters in the native bladder to form an incised native bladder;
   implanting a tissue flap comprising a nontubular bladder-expansion portion and a tubular portion into the incised native bladder; and
   suturing the non-tubular portion of the bladder-expansion portion to an edge of the incised native bladder; and
   anastomosing a distal end of the tubular portion of the tissue flap to the non-tailored end of each ureter;
   wherein the tissue flap is an ileal segment that is modified by cutting along an antimesenteric border of a native ileal segment to form a cut ileal segment with a detubularized first end with two cut edges and a second end that forms the tubular portion;
   wherein the method forms an augmented bladder with a volume capacity that is 100%-250% larger than a volume capacity of the native bladder; and
   wherein said anastomosing comprises an end-to-end anastomosis of one ureter to the distal end of the tubular portion and a side-to-end anastomosis of the other ureter to the distal end of the tubular portion.

2. The method of claim 1, further comprising detaching the two ureters from the native bladder after incising the native bladder and before implanting the tissue flap.

3. The method of claim 2, further comprising trimming a ureteral stenotic segment of each ureter to form a non-tailored end of each ureter.

4. The method of claim 1, wherein the tissue flap consists of an ileal segment that is 20-45 cm long and is taken from a distance of at least 10 cm from an ileocecal valve.

5. The method of claim 4 that further comprises:
   isolating the ileal segment such that a segmental blood supply of the ileal segment is retained and the ileal segment has two ends; and
   attaching a cut edge of the detubularized first end to itself to form the bladder-expansion portion of the tissue flap.

6. The method of claim 5, wherein the ileal segment has a length 26 cm to 38 cm and is taken at a distance of at least 10 cm from an ileocecal valve.

7. The method of claim 5, wherein the segment of the antimesenteric border of the ileal segment is 5 cm-8 cm in length.

8. The method of claim 1, wherein the nontubular bladder-expansion portion is a curved structure comprising a lumen-exposed surface which faces an interior of the augmented bladder and a peritoneum-exposed surface which faces an exterior of the augmented bladder.

9. The method of claim 1, wherein the tubular portion of the tissue flap has a hollow cylindrical shape with an interior radius of 5 mm-10 mm, an interior surface comprising a lumen-exposed surface, which is continuous with a lumen-exposed surface of the bladder-expansion portion, and an exterior surface comprising a peritoneum-exposed surface which is continuous with a peritoneum-exposed surface of the bladder-expansion portion.

10. The method of claim 9, wherein the lumen-exposed surface of the bladder-expansion portion has a surface area of 25 $cm^2$-45 $cm^2$ and the lumen-exposed surface of the interior surface of the tubular portion is 5 $cm^2$-15 $cm^2$.

11. The method of claim 1, wherein the bladder expansion portion is sutured to an edge of the incised native bladder with absorbable sutures.

12. The method of claim 1, wherein the subject is a child who has a neurogenic bladder.

13. The method of claim 1, wherein the subject is a child who has a posterior urethral valve bladder disorder.

14. The method of claim 1, wherein a proximal 5 cm of the ileal segment is kept as an afferent isoperistaltic tubularized loop.

15. The method of claim 1, wherein a detubularized segment of the ileum is constructed as a U- or W-shaped patch.

16. The method of claim 1, wherein the anastomosing a distal end of the tubular portion of the tissue flap to the non-tailored end of each ureter comprises an end-to-side anastomosis of a left ureter and an end-to-end anastomosis of a right ureter.

17. The method of claim 1, wherein the tubular portion of the tissue flap is a hollow cylindrical shape that has an interior ranging from 5-10 mm and a lumen-exposed interior surface of 5-10 $cm^2$.

18. The method of claim 1, further comprising growing the tissue flap on a biocompatible scaffold.

* * * * *